(12) United States Patent
Bridges et al.

(10) Patent No.: US 6,872,862 B2
(45) Date of Patent: Mar. 29, 2005

(54) PROPYLENE PRODUCTION

(75) Inventors: Robert S. Bridges, Friendswood, TX (US); Donald H. Powers, Pearland, TX (US); Steven T. Coleman, Humble, TX (US)

(73) Assignee: Equistar Chemicals, LP, Houston, TX (US)

( * ) Notice: Subject to any disclaimer, the term of this patent is extended or adjusted under 35 U.S.C. 154(b) by 14 days.

(21) Appl. No.: 10/606,026

(22) Filed: Jun. 25, 2003

(65) Prior Publication Data

US 2004/0267067 A1 Dec. 30, 2004

(51) Int. Cl.$^7$ ................................................ C07C 6/04
(52) U.S. Cl. ........................ 585/324; 585/331; 585/332; 585/643; 585/646; 585/664; 585/671
(58) Field of Search ................................. 585/324, 331, 585/643, 640, 664, 671

(56) References Cited

U.S. PATENT DOCUMENTS

| | | | |
|---|---|---|---|
| 3,326,866 A | 6/1967 | Haag ........................ 260/79.3 |
| 3,962,367 A | 6/1976 | Germanas et al. ....... 260/683.2 |
| 4,692,430 A | 9/1987 | Welch ........................ 502/342 |
| 4,962,267 A | 10/1990 | Slaugh ....................... 585/670 |
| 4,992,612 A | 2/1991 | Suzukamo et al. ......... 585/664 |
| 4,992,613 A | 2/1991 | Brownscombe ............. 585/666 |
| 5,157,196 A * | 10/1992 | Crossland et al. .......... 585/720 |
| 5,898,091 A | 4/1999 | Chodorge et al. .......... 585/647 |
| 5,955,397 A | 9/1999 | Didillon et al. ............ 502/339 |
| 6,111,160 A | 8/2000 | Powers et al. ............. 585/671 |
| 6,323,384 B1 | 11/2001 | Powers et al. ............. 585/671 |
| 6,358,482 B1 | 3/2002 | Chodorge et al. .......... 422/189 |
| 6,495,732 B1 | 12/2002 | Hearn et al. ............... 585/664 |
| 6,743,958 B2 * | 6/2004 | Commereuc et al. ....... 585/324 |

OTHER PUBLICATIONS

"Industrial Aspects of the Disproportionation Reaction," by R. L. Banks, *Journal of Molecular Catalysis*, vol. 8, p. 269–276, 1980, ISSN 0304–5102.

"Discovery and Development of Olefin Disproportionation (Metathesis)" by Robert L. Banks, American Chemical Society Symposium, Series, No. 222, Heterogeneous Catalysis: Selected American Histories, B.H. Davis and W. P. Hettinger, Jr., Editors, *American Chemical Society*, 1983, ISSN 0097–6156.

* cited by examiner

*Primary Examiner*—Thuan Dinh Dang
(74) *Attorney, Agent, or Firm*—Roderick W. MacDonald

(57) ABSTRACT

A method for making propylene from alpha olefins, internal linear olefins and isoolefins wherein the alpha olefins are subjected to a combination of hydrogenation and double bond isomerization to form additional internal linear olefins, the internal linear olefins are separated from the isoolefins and disproportionated with ethylene to form a propylene product, while the thus separated isoolefins are subjected to skeletal isomerization to form yet additional internal linear olefins to be converted into yet additional propylene product.

12 Claims, 1 Drawing Sheet

PROPYLENE PRODUCTION

BACKGROUND OF THE INVENTION

1. Field of the Invention

This invention relates to a method for making propylene utilizing hydrocarbons that have four carbon atoms per molecule ($C_4$'s). More particularly this invention relates to a process for forming propylene from an isobutylene containing feedstock.

2. Description of the Prior Art

Although this invention will, for the sake of clarity of understanding, be described in the context of an olefin production plant (olefin plant), this invention is broadly applicable to the use, as feed thereto, of any hydrocarbon stream containing the requisite feed component(s) as described in detail herein.

Thermal cracking of hydrocarbons is a petrochemical process that is widely used to produce olefins such as ethylene, propylene, butenes, butadiene, and aromatics such as benzene, toluene, and xylene. In an olefin plant, a hydrocarbon feedstock such as naphtha, gas oil, or other fractions of whole crude oil is mixed with steam which serves as a diluent to keep hydrocarbon molecules separated. This mixture, after preheating, is subjected to severe hydrocarbon thermal cracking at elevated temperatures (1450° F. to 1550° F.) in a pyrolysis furnace (steam cracker).

The cracked effluent product from the pyrolysis furnace contains gaseous hydrocarbons of great variety (from 1 to 35 carbon atoms per molecule). This effluent contains hydrocarbons that are aliphatic, aromatic, saturated, and unsaturated, and can contain significant amounts of molecular hydrogen (hydrogen).

The cracked product of a pyrolysis furnace is then further processed in the olefin plant to produce, as products of the plant, various separate individual product streams of high purity such as hydrogen, ethylene, propylene, mixed hydrocarbons having four carbon atoms per molecule (crude $C_4$'s), and pyrolysis gasoline. It is this crude $C_4$ product of the debutanizer of an olefin plant upon which is focused this description of one embodiment within this invention.

Crude $C_4$'s can contain varying amounts of n-butane (butane), isobutane, butene-1, butene-2, isobutylene (isobutene), acetylenes, butadiene, and hydrogen. The term butene-2 as used herein includes cis-butene-2, trans-butene-2, or a mixture of both.

Heretofore crude $C_4$'s have been subjected to butadiene extraction or butadiene selective hydrogenation to remove most, if not essentially all, of the butadiene and acetylenes present. Thereafter the crude $C_4$ raffinate was subjected to an etherification process wherein the isobutylene was converted to methyl tertiary butyl ether (MTBE).

Also heretofore crude $C_4$'s have been subjected to selective hydrogenation of dioelfins (butadiene) with simultaneous isomerization of alpha olefins (butene-1) to internal olefins (butene-2) followed by etherification of the isoolefins (isobutylene to MTBE), and finally metathesis of internal olefins (butene-2) with ethylene to produce propylene, see U.S. Pat. No. 5,898,091 to Chodorge et al.

In addition, catalytic distillation of various hydrocarbon streams for various purposes such as hydrogenation, monoolefin isomerization, etherification, dimerization, hydration, dissociation, and aromatic alkylation has been disclosed, see U.S. Pat. No. 6,495,732 B1.

Finally, olefinic $C_4$'s have been converted to propylene and isobutene using selective hydrogenation plus double bond isomerization of butene-1 to butene-2, followed by separation of isobutene from the butene-2, and metathesis of the butene-2 with ethylene to form propylene, see U.S. Pat. No. 6,358,482.

If MTBE market demand should decline, it is desirable to be able to utilize the isobutylene that was formerly used in producing MTBE to produce a different product that is enjoying more robust market demand.

It has been suggested that the isobutylene be dimerized to iso-octene followed by hydrogenation to iso-octane, or be alkylated to iso-octane, neither of which promises to be a cost-effective solution.

SUMMARY OF INVENTION

In accordance with this invention, not only are the internal olefins in a feedstock converted into propylene, but, in addition, the isobutylene in that feedstock and, depending on the recycle route chosen, the alpha olefins associated with such isobutylene, is converted into additional internal olefins thereby substantially increasing the yield of propylene from a given (original) feedstock. This is a substantial advantage over and not suggested nor rendered obvious by the prior art. For example, U.S. Pat. No. 6,358,482 merely suggests that the isobutene recovered from its process can be used in various fashions. This is not a suggestion, even to one skilled in the art, to increase the yield of propylene from a specific feedstock by the skeletal isomerization of the isoolefins in that feedstock.

Other unobvious advantages for the process of this invention over the disclosures of the prior art will be described hereinafter in detail.

In the context of an olefin plant, an increase in the output of propylene product from that plant while using the same feedstock is a distinct advantage in a robust propylene market.

Yet another unsuggested advantage for this invention is that, in addition to producing more propylene from the same olefin containing feedstock, this invention produces a $C_5$ and heavier olefin product that is employed in the automotive gasoline pool.

DETAILED DESCRIPTION OF THE INVENTION

Figure 1:
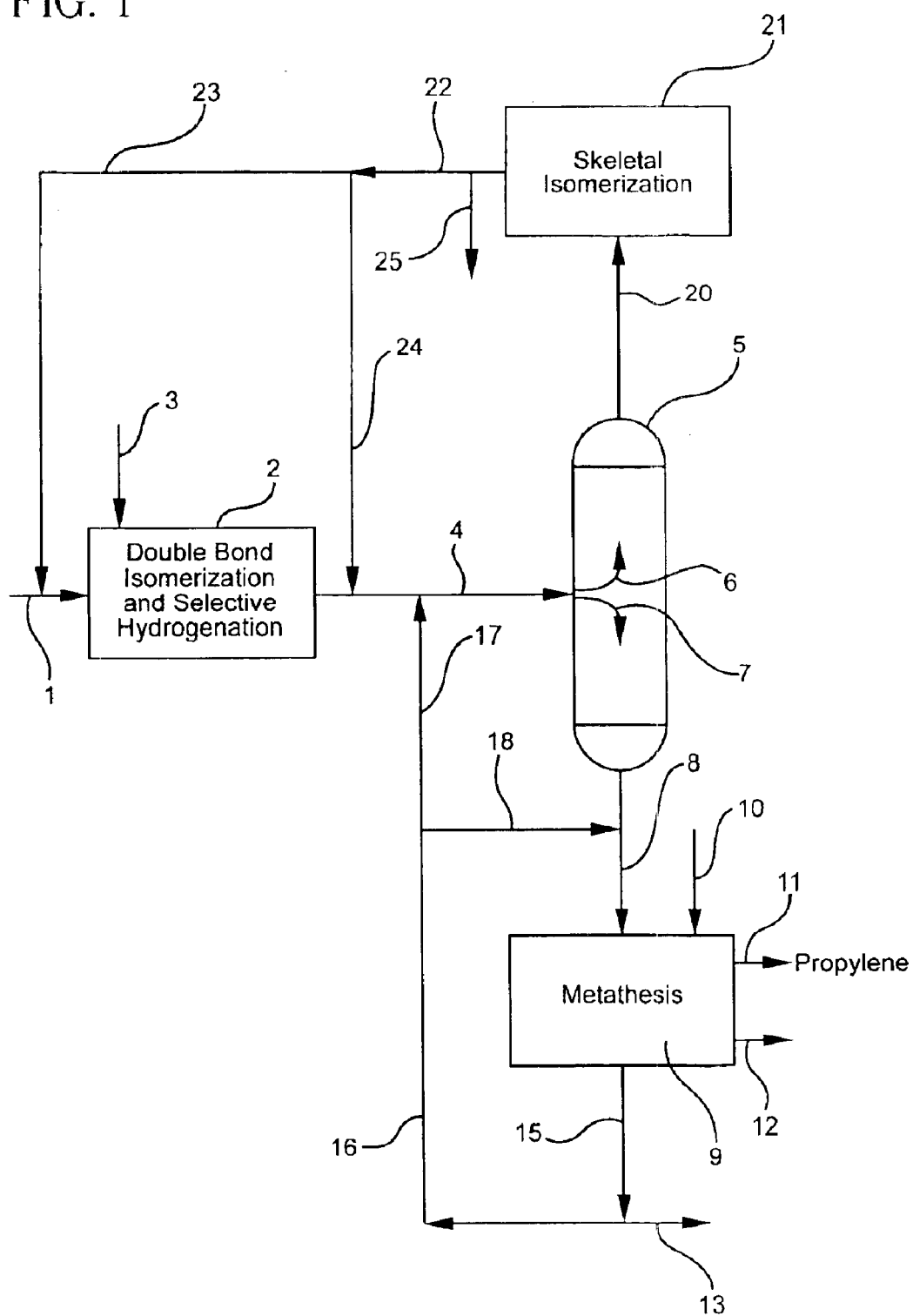
FIG. 1 shows a schematic flow diagram of one embodiment within this invention.

By this invention, and referring to FIG. 1, a feedstock 1 containing in whole or in part a first mixture composed of alpha olefins (linear alpha olefins), internal linear olefins (internal olefins), and isoolefins all having four carbon atoms per molecule is first subjected to a combination operation (zone) 2 wherein double bond isomerization conditions are present that convert (transform) at least part of the alpha olefins to internal linear olefins and at the same time diolefins and acetylenes present in the feedstock, if any, are selectively hydrogenated to produce, at least in part, additional alpha and internal linear olefins. Hydrogen is provided to zone 2 by way of line 3 for the selective hydrogenation part of the process of zone 2.

The product of operation 2 is a second mixture that is substantially enriched in internal linear olefins and essentially free of diolefins and acetylenes, but still contains isoolefins and alpha olefins. This product is passed by way of line 4 to a distillation zone 5 wherein the isoolefins and alpha olefins 6 are separated from the internal linear olefins 7.

Internal linear olefins 7 are recovered as tower 5 bottoms and passed by way of line 8 to zone 9 wherein olefins 7 are subjected to disproportionation conditions (metathesis) in the presence of ethylene, provided by way of line 10, to form propylene. The propylene product of the process of this invention is recovered by way of line 11 for other disposition. A $C_5$ (5 carbon atom molecules) and heavier (plus) olefin product is separately recovered by way of line 12. Unreacted internal linear olefins are recovered from zone 9 by way of line 15 and can be recycled to either or both of tower 5 and zone 9, as desired, by way of lines 16 and 17 or lines 16 and 18, respectively.

An overhead product is recovered from tower 5 by way of line 20 and passed into zone 21 which maintains skeletal isomerization conditions which favor the conversion of isoolefins to a chemical equilibrium mixture of alpha olefins and internal linear olefins. A significant advantage of this invention is that overhead product 20 is, because of the distillation effected in zone 5, substantially enriched in isoolefin content. Thus, stream 20 has a very favorable ratio of isoolefins to alpha and internal linear olefins to allow a skeletal isomerization operation 21 to function to form substantial additional quantities of alpha olefins and desirable internal linear olefins before reaching the normal chemical equilibrium constraints between isoolefins, alpha olefins, and internal linear olefins.

The product of zone 21 is substantially enriched in internal linear olefin content over stream 20. At least part of this internal linear olefin content is new to and was not originally present in feedstock 1 thereby providing for the production of more (net) internal linear olefins than would be possible from feedstock 1 without the use of zone 21. This internal linear olefin enriched stream which contains net production of internal linear olefins not in original feedstock 1 in turn provides for net production of propylene product 11 that would not otherwise have been recovered from the original chemical composition of feedstock 1.

Product stream 22 is a third mixture that can be returned as co-feed to either zone 2 by way of lines 22 and 23 for the conversion of at least part of its alpha olefin content to yet additional internal linear olefins that were not present in feedstock 11 and/or zone 5 by way of lines 22 and 24 so that the net internal linear olefin content in stream 22 can be passed to zone 9 for net propylene production over that which was possible by utilizing feedstock 1 by itself and without benefit of the process of zone 21.

If desired, at least part of third mix 22 can be separately removed from zone 21 by way of line 25 for various reasons. For example, if isoaliphatics are present in feedstock 1 they are non-reactive in this process and tend to build up in the system shown in FIG. 1. Accordingly, stream 25 can be taken as a purge stream to relieve the isoaliphatic build up in the system. In addition, or alternatively, the third mixture in stream 25 could be employed in a known process that will alkylate its isoaliphatic content with the olefin content, such as alpha and internal $C_4$'s, to form an automotive gasoline alkylate of mixed isooctanes plus a separate $C_4$ stream product.

The feedstock (feed) or first mixture 1 for this invention can be any suitable stream that contains the requisite $C_4$ components. One such stream is a high purity isobutylene stream that contains no n-butane or isobutane. Such a stream can be obtained as a byproduct of a propylene oxide production process. This feed is passed into zone 2 which is a combination of a double bond isomerization zone (reactor) and a selective hydrogenation zone (reactor) so that the feed components, upon entering zone 2 are subjected in a single operation both to selective hydrogenation conditions, and double bond isomerization conditions in that zone.

Other suitable feeds include raffinate products obtained from the extractive distillation of crude $C_4$'s with a solvent that preferentially removes diolefins such as butadiene by altering the relative volatility of the butadiene, or the selective hydrogenation of $C_4$'s to convert butadiene and acetylenes to butenes. These raffinate products (sometimes called raff-1 and super raff-1) are depleted (less than about 1 weight percent (wt. %), based on the total weight of the raffinate) in butadiene and acetylenes content, but rich (over 75 wt. % on the same basis) in a mixture of butene-1, butene-2, and isobutylene—all desired components for the process of this invention. The small amount of butadiene left in a raffinate product can be readily hydrogenated in zone 2. Another suitable feed is a crude $C_4$ stream from an olefin plant debutanizer as described herein. This feed requires conventional hydrogenation of its butadiene and acetylenes content before it is passed into tower 5, because the butadiene content of the feed to zone 21 is preferably less than 100 parts per million (ppm).

In zone 2 alpha olefins such as butene-1 are transformed as to the location of their double bond without affecting the carbon atom skeleton (chain) thereof. Thus, straight chain (linear) butene-1 is converted to straight chain (linear) butene-2. This conversion proceeds up to the normal chemical equilibrium constraint of a mixture of alpha and internal olefins. Newly formed internal linear olefins are thus made available for conversion to propylene along with the internal linear olefins that were originally present in feedstock 1.

Zone 2 carries, at least, one catalyst effective for double bond isomerization. This same catalyst system can also be effective as a selective hydrogenation catalyst which promotes not only double bond isomerization, but also hydrogenation of diolefins and acetylenes at least in part to monoolefins if hydrogen is available. Hydrogen can be added to the process, if insufficient hydrogen is present in feedstock 1, by way of line 3 up to about 1 wt. % based on the total weight of the feed, greater amounts of hydrogen tending to reduce the selectivity of the catalyst for selective hydrogenation of diolefins and acetylenes. For example, while an alpha olefin such as butene-1 is converted at least in part to an internal linear olefin such as butene-2 in zone 2, at the same time butadiene and acetylenes such as vinyl acetylene are selectively hydrogenated to a mixture of butene-1 and butene-2.

The resulting reaction product is a second mixture in line 4 which is rich in, for example, butene-1 and butene-2, but with significant amounts of isobutylene, and containing essentially no butadiene or acetylenes. Second mixture 4 can also contain either or both of unreactive n-butane and isobutane.

Stream 4 is passed into zone 5 which can, for example, be a conventional butene splitter which readily separates, in well known manner, butene-1 from butene-2. Contrary to the ease of separating butene-1 from butene-2 by simple distillation, butene-1 and isobutylene cannot be economically separated by simple distillation since their boiling points differ by only 0.6° C. Isobutylene present in stream 4 will be recovered overhead in line 20 of tower 5 along with the separated butene-1. In addition, isobutane, being lighter boiling as well, will be recovered in the overhead.

Internal linear olefins such as butene-2 and most of the n-butane present will be recovered as bottoms product in line 8 of tower 5.

Overhead stream 20 is passed to zone 21 for the conversion of isoolefins such as isobutylene to an equilibrium mixture of monoolefins, i.e., butene-1 and butene-2, thereby producing new (net) butene-2, in addition to that produced in zone 2, for later conversion to additional net propylene by way of zone 9.

The product of zone 21 is a third mixture found in line 22 which can contain one or more of alpha olefins, linear internal olefins, unconverted isoolefins and isoaliphatics. This third mixture 22 is useful in and returned to either or both of zones 2 and 5 by way of lines 23 and 24, respectively, to generate additional net linear internal olefin in zone 2, and, ultimately, net additional propylene from zone 9.

It should be noted here that in this invention, skeletal isomerization in zone 21 is distinguished from double bond isomerization in zone 2 in that skeletal isomerization involves the movement of a carbon atom to a new location on the carbon atom skeleton of the molecule, e.g., from a branched isobutylene skeleton to a linear or straight chain (not branched) butene skeleton. Double bond isomerization does not involve movement or shifting of carbon atoms on the skeleton, but rather only involves movement of a double bond within the existing skeleton while the carbon atoms that form the carbon atom skeleton remain in their original locations in that skeleton.

Since isoaliphatics such as isobutane, if present in the feed stream, are not reactive in this process, they will build up in line 22 of skeletal isomerization zone 21. Accordingly, a purge stream 25 can be taken from stream 22 to relieve isobutane buildup and can be employed elsewhere. For example, since this purge stream can contain isobutane, alpha olefins, and internal linear olefins, it could be employed to advantage in an alkylation process to form a gasoline grade alkylate of mixed isooctanes.

Normal butane and internal linear olefins are recovered at the bottom of tower 5 as shown by arrow 7 for recovery therefrom by way of line 8, and for use as feed for metathesis zone 9. In zone 9 butene-2 and ethylene co-feeds are metathesised to propylene product, 1 mole of butene-2 and 1 mole of ethylene yielding 2 moles of propylene.

The metathesis reaction yields useful byproducts. One such byproduct is a mixed olefinic stream 12 that contains hydrocarbons of 5 carbon atoms per molecule and heavier that are in the automotive gasoline boiling range (from about 77° F. to about 437° F.). For example, this byproduct can contain a substantial majority (up to 80 wt. % or more) $C_5$ olefins, and a significant minority (up to 20 wt. %) $C_6$ and heavier olefins, all wt. % based on the total weight of the byproduct.

Normal butane, if present in the feed, being unreactive in the process of this invention, also tends to build up in the system. Stream 13 can be taken as a purge stream from the process, in whole or in part. Stream 13 is a useful byproduct in that it contains any unreacted butene-2 as well as n-butane, and can be used in alkylation to form gasoline grade alkylate of mixed isooctanes plus a separate butane product. Removal of stream 13 helps relieve n-butane build-up in the system caused by recycle of the unreacted n-butane within the metathesis process. Alternatively, stream 15 can, in whole or in part, be recycled as co-feed to tower 5 such as by introduction into stream 4 and/or metathesis zone 9 such as by introduction into stream 8. This way, butene-2 that was not disproportionated with ethylene in its first pass through zone 9 is returned to the process for another pass through that zone. If stream 15 is recycled in its entirety as an additional source of butene-2 for zone 9, a purge stream (not shown) can be taken from stream 15 and removed from the process in order to relieve n-butane build-up in the system.

The selective hydrogenation/double bond isomerization conditions within zone 2 can be a temperature of from about 70° F. to about 270° F. and a pressure of from about 20 psig to about 400 psig and a weight hourly space velocity of from about 0.5 $h^{-1}$ to about 20 $h^{-1}$.

The catalyst or catalysts used in zone 2 can vary widely. If there is no appreciable (less than about 100 ppm) butadiene content in feed 1, the catalyst can be primarily only an isomerization component and need not contain a component (catalyst) that promotes the hydrogenation of butadiene. If there is appreciable butadiene content in the feed (greater than about 100 ppm and up to about 1 wt. % based on the total weight of the feed), the catalyst can additionally contain a hydrogenation component. If butadiene is present in the feed, the isomerization catalyst and hydrogenation catalyst can be employed in zone 2 either mixed with one another in a single catalyst bed in zone 2, or in separate discrete catalyst beds in zone 2, each discrete bed containing either solely isomerization catalyst or solely hydrogenation catalyst, or a dual function catalyst as explained herein below.

The isomerization catalyst employed in zone 2 effects and favors the formation of internal linear olefins over the formation of linear alpha olefins. Generally, the catalysts employed promote, preferably primarily promote, double bond shifts within a specific olefin molecule (double bond isomerization). The catalysts useful in this invention will be obvious to one skilled in the art since they are either commercially available or fully disclosed in the prior art. Such catalysts include acidic ion exchange resins such as sulfonated resins with sulfonic acid sites (U.S. Pat. No. 3,326,866), perfluorinated polymer sulfonic acid catalyst, phosphoric acid catalyst, carboxylic acid catalyst, fluorinated alkyl sulfonic acid catalyst, alumina plus alkali metal (U.S. Pat. No. 4,992,612), zinc aluminate (U.S. Pat. No. 4,692,430), zirconia, sulfated zirconia, cobalt/sulfur catalyst (U.S. Pat. No. 3,962,367), ruthenium oxide (U.S. Pat. No. 4,962,267), alumino phosphates, and zeolite structures with or without alkali metal (U.S. Pat. No. 4,992,613), and alumina or silica alumina.

The hydrogenation catalyst component employed in zone 2 favors the saturation with hydrogen of at least one, preferably one, double bond in a butadiene molecule, and similar saturation or partial saturation of acetylenes. These catalysts will also be obvious to one skilled in the art and commercially available. Such catalysts can contain a noble metal, e.g., at least one of palladium, platinum, and rhodium, either supported or unsupported. When the noble metal is supported on an acidic material, a combined (dual) function catalyst of double bond isomerization and selective hydrogenation is achieved. Suitable catalysts having both a double bond isomerization and a hydrogenation capability will be obvious to those skilled in the art, and include, but are not limited to, at least one of palladium, platinum, and rhodium carried on an acidic support such as alumina, silica alumina, and the like. The noble metal(s) can be present in the catalyst in amounts of from about 0.1 to about 0.3 wt. % based on the total weight of the catalyst. For other suitable catalysts for both hydrogenation and double bond isomerization, see U.S. Pat. Nos. 5,955,397 and 6,495,732 B1.

The metathesis zone 9 operating conditions can vary widely, but are generally a temperature of from about 300°

F. to about 800° F., a pressure of from about 200 psig to about 600 psig, and a weight hourly space velocity of from about 1.0 h$^{-1}$ to about 100 h$^{-1}$.

Suitable catalysts that promote, preferably primarily promote, metathesis as described herein are known in the art, and include at least one of halides, oxides and/or carbonyls of at least one of molybdenum, tungsten, rhenium and/or magnesium carried on a support such as silica and the like. The conversion of butene-2 in the presence of excess ethylene to propylene is known and has been demonstrated; see R. L. Banks, Journal of Molecular Catalysis, Vol. 8, p. 269–276, 1980, ISSN 0304-5102. For more information on olefin metathesis, see Discovery and Development of Olefin Disproportionation (Metathesis) by Robert L. Banks, American Chemical Society Symposium Series, No. 222, Heterogeneous Catalysis: Selected American Histories, B. H. Davis and W. P. Hettinger, Jr., Editors, American Chemical Society, 1983, ISSN 0097–6156.

The skeletal isomerization zone 21 operating conditions also vary widely, but generally are a temperature of from about 450° F. to about 1200° F., a pressure of from about 0 psig to about 150 psig, and a weight hourly space velocity of from about 1.0 h$^{-1}$ to about 50 h$^{-1}$. Skeletal isomerization catalysts useful in this invention are known in the art and include zeolites having one-dimensional pore structures with a pore size ranging from greater than about 0.42 nanometers (nm) and less than about 0.7 nm. This type of isomerization process is known, see U.S. Pat. No. 6,111,160 to Powers et al., and U.S. Pat. No. 6,323,384 also to Powers et al.

The distillation conditions for zone 5 can vary widely depending on the composition of the initial feedstock, but will generally be from about 20° F. to about 260° F. at a pressure of from about 0 psig to about 400 psig.

EXAMPLE

A raffinate-1 stream from a butadiene extraction unit consisting essentially of about 3 wt. % isobutane, about 40 wt. % isobutylene, about 27 wt. % butene-1, about 16 wt. % butene-2, about 1 wt. % butadiene, and about 13 wt. % n-butane, all wt. % based on the total weight of the stream, is employed as feed to zone 2 shown in the drawing with a double bond isomerization/hydrogenation catalyst bed carried in zone 2. The isomerization conditions are about 123° F. and about 70 psig. The double bond isomerization/hydrogenation catalyst is a commercially available catalyst composed of 0.2 wt. %, based on the total weight of the catalyst, of palladium on a silica/alumina support.

The distillation conditions in tower 5 are set to fractionally distill butene-2 from butene-1 and isobutylene so that butene-1 and isobutylene will be recovered overhead, and butene-2 will be recovered as tower bottoms. Under such distillation conditions, isobutane and isobutylene rise with butene-1, while the majority of the n-butane travels downwardly with the butene-2.

The distillation conditions are set with a tower top temperature and pressure of about 108° F., and about 65 psig, a reflux ratio of about 10, and 200 valve trays in the tower, which yields a tower bottom temperature of about 144° F. and pressure of about 80 psig.

A mixture of n-butane and butene-2 containing about 84 wt. % butene-2, based on the total weight of the mixture, is removed from the tower bottom and passed by line 8 to metathesis zone 9 wherein it is contacted with a molar excess of ethylene in the presence of a commercially available metathesis catalyst composed of a mixture of tungsten oxide and magnesium oxide at a temperature of about 550° F. and pressure of about 300 psig. Two products are recovered from zone 9, a propylene stream at 11, and a separate gasoline grade stream at 12 containing about 80 wt. % $C_5$ olefins based on the total weight of the stream with the remainder being essentially $C_6$ and higher olefins boiling within the automotive gasoline range aforesaid.

In zone 2, butene-1 is transformed to butene-2, and the newly formed butene-2 is ultimately employed as additional feed material for the metathesis reaction zone 9.

Butadiene is selectively hydrogenated in zone 2 to a mixture of butene-1 and butene-2, the newly formed butene-2 also being used ultimately in metathesis feed 8.

Newly formed butene-1 from butadiene hydrogenation, existing butene-1 that was not converted to butene-2, isobutane, and isobutylene, all in zone 5, are recovered, due to the prevailing distillation conditions, at the tower top where they are collected and transferred by way of line 20 to skeletal isomerization zone 21.

In zone 21 the primary reaction is the transformation of branched isobutylene to linear butenes (-1 and -2). A secondary reaction is double bond isomerization of butene-1 to butene-2. Accordingly, the product of zone 21 is a mixture of butene-2 (newly formed and unconverted), butene-1, unconverted isobutylene, and isobutane. This product is recycled by way of lines 22 and 23 as co-feed to zone 2 to make yet more butene-2 from butene-1 in zone 2, and separation of existing and newly formed butene-2 for use in the metathesis operation for producing net additional propylene product. The isobutylene in recycle stream 22 ultimately reaches skeletal isomerization zone 21 again at which time at least part of it is converted to a mixture of butenes.

On a single pass basis, and with no recycle, about 65 wt. percent of the butene-2 in stream 8 is converted to either propylene or gasoline, with about 90 percent selectivity to propylene. In the skeletal isomerization operation, also on a single pass basis, there is about a 50 wt. percent conversion of isobutylene with a 90 percent selectivity to butene-1 and butene-2.

It can be seen from the foregoing example that the process of this invention is replete with opportunities throughout the entire process to make newly formed net butene-2 which is then made into net propylene product. Accordingly, it can be seen that the process of this invention is highly leveraged toward and very efficient in making new butene-2. Thus, in addition to making propylene out of the butene-2 originally in the feedstock to the process, this invention significantly increases the amount of propylene product obtained from a given feed based on the butene-2 content of the original feed.

Reasonable variations and modifications are possible within the scope of this disclosure without departing from the spirit and scope of this invention.

We claim:

1. A method for forming propylene comprising providing a feedstock containing at least in part a first mixture of hydrocarbons comprising alpha olefins, internal linear olefins, and isoolefins having four carbon atoms per molecule, introducing said feedstock into a combination hydrogenation/double bond isomerization zone wherein (1) any diolefins and acetylenes that may be in said feedstock are converted at least in part to alpha and internal linear olefins, and (2) at least part of said alpha olefins in said feedstock and at least part of said alpha olefins formed by said hydrogenation are converted to additional internal linear olefins thereby producing as a product of said combination zone a second mixture that is enriched in internal linear olefins, passing said second mixture into a distillation zone wherein said second mixture is split into an overhead fraction that is enriched in alpha olefins and isoolefins, and a bottoms fraction that is enriched in internal linear olefins, passing said overhead fraction into a skeletal isomerization zone wherein said isoolefins are converted at least in part to additional internal linear olefins to form a third mixture that is enriched in internal linear olefins, returning said third mixture as co-feed to said distillation zone for the separation of internal linear olefins in said third mixture into said bottoms fraction, passing said bottoms fraction and ethylene into a metathesis zone which favors the disproportionation of internal olefins with ethylene to produce propylene as a product of the process and a separate gasoline grade olefin product, and removing at least one purge stream from at least one of said skeletal isomerization zone and said metathesis zone and employing said at least one purge stream in an alkylation zone to form an alkylate of mixed isooctanes.

2. The method of claim 1 wherein said internal linear olefins recovered from said metathesis zone are returned as co-feed to said distillation zone.

3. The method of claim 1 wherein said first mixture contains at least in part butene-1, butene-2, and isobutylene, said combination zone contains at least one catalyst that promotes the selective hydrogenation of butadiene and vinyl acetylenes, and the formation of butene-2 from butene-1, butene-2 is recovered in said bottoms fraction, said metathesis zone contains at least one catalyst that promotes the disproportionation of butene-2 with ethylene to form propylene, said overhead fraction contains butene-1 and isobutylene, said skeletal isomerization zone contains at least one skeletal isomerization catalyst that promotes the conversion of isobutylene to a mixture of butene-1 and butene-2, said mixture of butene-1 and butene-2 along with any unconverted isobutylene being recovered from said skeletal isomerization zone as said third mixture, and said third mixture is returned as co-feed to said distillation zone.

4. The method of claim 3 wherein said combination zone operating conditions are a temperature of from about 70° F. to about 270° F., a pressure of from about 20 psig to about 400 psig, and a weight hourly space velocity of from about 0.5 $h^{-1}$ to about 20 $h^{-1}$.

5. The method of claim 3 wherein said distillation zone operating conditions are a temperature of from about 20° F. to about 260° F. and a pressure of from about 0 psig to abut 400 psig.

6. The method of claim 3 wherein said metathesis zone operating conditions are a temperature of from about 300° F. to about 800° F., a pressure of from about 200 psig to about 600 psig, and a weight hourly space velocity of from about 1 $h^{-1}$ to about 100 $h^{-1}$.

7. The method of claim 3 wherein said skeletal isomerization operating conditions are a temperature of from about 450° F. to about 1,200° F., a pressure of from about 0 psig to about 150 psig, and a weight hourly space velocity from about 1 $h^{-1}$ to about 50 $h^{-1}$.

8. The method of claim 3 wherein said combination zone catalyst is at least one of palladium, platinum, nickel, and rhodium carried on an acidic support.

9. The method of claim 3 wherein said metathesis zone catalyst is at least one of halides, oxides, and carbonyls of at least one of molybdenum, tungsten, rhenium, and magnesium carried on a support.

10. The method of claim 3 wherein said skeletal isomerization zone catalyst is at least one zeolite having one dimensional pore structures with a pore size ranging from greater than about 0.42 nm and less than about 0.7 nm.

11. The method of claim 1 wherein said feed stock contains, in addition to said first mixture, butadiene, vinyl acetylene, n-butane, isobutene, and hydrogen; in said distillation zone said n-butane separates with said butene-2 and both n-butane and butene-2 are passed to said metathesis zone; in said distillation zone said isobutylene, butene-1, and isobutane separate from said n-butane and butene-2 and are passed to said skeletal isomerization zone, said third mixture product of said skeletal isomerization zone that is returned as co-feed to said distillation zone contains butene-1, butene-2, isobutylene, and isobutane, said butadiene and vinyl acetylene in said first mixture are hydrogenated at least in part in said double bond isomerization zone to at least a mixture of butene-1 and butene-2, and said butene-1 in said first mixture is converted at least in part in said double bond isomerization zone to butene-2.

12. The method of claim 11 wherein a purge stream containing at least one of n-butane, butene-1, butene-2 and isobutane is removed from at least one of said skeletal isomerization zone and said metathesis zone and employed in an alkylation zone to form an alkylate of mixed isooctanes.

* * * * *